United States Patent [19]

Siddiqi et al.

[11] Patent Number: 4,956,276

[45] Date of Patent: Sep. 11, 1990

[54] ANALYTICAL METHOD OF DETERMINING A REDUCED CO-ENZYME

[75] Inventors: Igbal Siddiqi, Geneva, Switzerland; Jean Brochot, Saint Julien en Genevois, France

[73] Assignee: Battelle Memorial Institute, Geneva, Switzerland

[21] Appl. No.: 939,123

[22] PCT Filed: Mar. 10, 1986

[86] PCT No.: PCT/CH86/00032

§ 371 Date: Nov. 13, 1986

§ 102(e) Date: Nov. 13, 1986

[87] PCT Pub. No.: WO86/05517

PCT Pub. Date: Sep. 25, 1986

[30] Foreign Application Priority Data

Mar. 15, 1985 [CH] Switzerland .......................... 1165/85

[51] Int. Cl.$^5$ .................... C12Q 1/58; C12Q 1/54; C12Q 1/32; C12Q 1/28
[52] U.S. Cl. ........................... 435/12; 435/14; 435/15; 435/26; 435/28
[58] Field of Search .................. 435/28, 26, 14, 12, 435/15

[56] References Cited

U.S. PATENT DOCUMENTS

| 4,353,983 | 10/1982 | Siddiqi | 435/11 |
| 4,551,427 | 11/1985 | Draeger et al. | 435/14 |
| 4,608,335 | 8/1986 | Fossati | 435/12 |

FOREIGN PATENT DOCUMENTS

| 0079792 | 5/1983 | European Pat. Off. | 435/12 |
| 0124909 | 11/1984 | European Pat. Off. | |
| 2547925 | 12/1984 | France | 435/14 |
| 6124397 | 9/1981 | Japan | 435/14 |
| 0140899 | 11/1981 | Japan | 435/14 |
| 0151900 | 8/1984 | Japan | 435/12 |

OTHER PUBLICATIONS

Siddiqi, Clin. Chem., vol. 28/9, 1982, p. 1962–1967.

*Primary Examiner*—Esther M. Kepplinger
*Assistant Examiner*—Florina B. Hoffer
*Attorney, Agent, or Firm*—Cushman, Darby & Cushman

[57] ABSTRACT

The sample for analysis containing the co-enzyme to be detemined, inter alia NADH or NADPH, is placed in the presence of a fluorinated aromatic compound. In the presence of oxygen and peroxidase, the fluorinated compound releases fluoride ions at a rate proportional to the quantity of co-enzyme to be determined. The thus-formed $F^-$ ions are determined, thus obtaining the desired result.

10 Claims, 2 Drawing Sheets

ANALYTICAL METHOD OF DETERMINING A REDUCED CO-ENZYME

The invention relates to biological analysis, more particularly to the determination of co-enzymes in which the molecule contains nicotinamide, inter alia NADH, NADPH and APADH.

As is known, these abbreviations denote the following substances:

NADH=reduced form of NAD (or NAD+) (nicotinamideadenine-dinuclotide) also called co-enzyme I or DPN (diphosphopyridine nucleotide)

NADPH=reduced form of NADP (nicotinamideadenine-dinucleotide phosphate) also called co-enzyme II or TPN (triphosphopyridine nucleotide)

APADH=reduced form of APAD (acetyl-pyridineadenine-dinucleotide).

The structure of NAD is made up in succession of a 3-amidopyridinium group fixed in the 1-position of a ribose unit connected by its -5- position to a diphosphate group fixed at -5'- to a second ribose group comprising an adenine group at -1'-.

The reversible conversion of NAD to NADH is diagrammatically represented as follows (where R denotes the ribose-diphosphate-ribose-adenine chain):

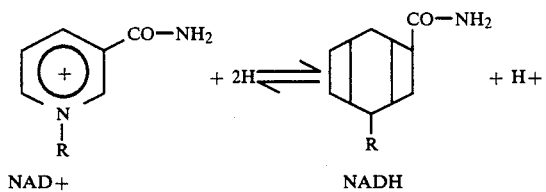

Nicotinamide co-enzymes play a part in a large number of biochemical enzymatic reactions used as clinical tests. These include oxidation of alphahydroxyacids to the corresponding ketonic acids in the presence of a suitable dehydrogenase. One example is the oxidation of lactic acid or lactates to pyruvic acid

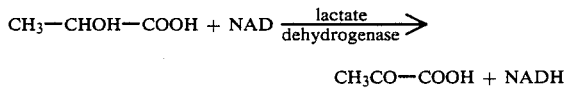

Similarly glucose-6-phosphate is oxidised in the presence of NAD and glucose-6-phosphate dehydrogenase (G6PDH) to glucono-δ-lactone-6-phosphate and NADPH. The determination of NADP or NADPH in this reaction is very important since it can be indirectly, used to determine glucose in biological fluids after it has been converted to glucose-6-phosphate in the presence of ATP (adenosine triphosphate) and hexokinase.

NADH also acts as a co-enzymatic factor in the conversion by ammonium salts of 2-oxoglutarate to L-glutamate in the presence of GLDH (glutamade dehydrogenase), so that the ammonium in the reaction medium can be determined by determining the remaining NADH (or the NAD+ formed). This reaction is of use for determining urea in biological fluids which, in the presence of urease, supply the $NH_3$ occurring as the $NH_4$ ion in the aforementioned conversion.

Other applications associated with the determination of the NAD+, NADH and APADH factors are described in the following documents: EP-A-29 104 (MILES), FR-A-2 299 644 (AKZO).

In view of the great importance of determining the aforementioned co-enzymes in one or the other of their states of oxido-reduction, numerous techniques have been proposed for this purpose.

For example, since NAD and NADH have different absorptions in UV, one form can be determined in the presence of the other by spectrophotometry. The sensitivity of spectrophotometric determination can also be increased by combined use of coloured redox compounds, e.g. tetrazolium compounds which, in the presence of NADH or NADPH and an electron acceptor such as phenazine methosulphate, give intensely coloured formazan salts. (See e.g. document EP-A-114 267). Use may also be made of fluorimetric techniques as described e.g. in document FR-A-2 266 644.

An electrochemical method may also be used as described in document J 56 035 050, where NADH or NADPH is oxidized by Meldola blue, after which the reduced form of the dye is oxidized electrochemically and the oxidation current is measured.

It has recently been recommended (EP-A-29 104) to use the following reaction:

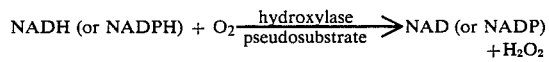

The resulting released hydrogen peroxide is then determined by conventional methods, e.g. by its action, catalyzed by peroxidase, on a redox indicator, the oxidised form whereof is determined by colorimetry.

Document EP-A-124 909 describes a process which is similar but simplified since peroxidase is the only enzyme involved. The method consists in reacting the co-enzyme with peroxidase in the presence of metal ions such as $Mn^{+2}$ or $Co^{+2}$, resulting in quantitative formation of hydrogen peroxide which is then determined as before by conventional methods, e.g. by colorimetry, inter alia the system comprising 4-aminoantipyrine as coupler and a phenolic compound or an aromatic amine as the chromophore. In the absence of metal ions (see page 5, paragraph 1 of this document) the formation of $H_2O_2$ is not quantitative and consequently the reaction has no analytical use.

Although colorimetric techniques are very attractive, they use of use only in a colourless, optically transparent medium, which is far from being the case with most biological fluids for analysis. It is also relatively complicated to apply and is usually not as sensitive as electrometric techniques. In this connection the present applicants have recently disclosed (see EP-A-20 623) that excellent results with regard both to sensitivity and accuracy of measurement are obtained in the analysis of $H_2O_2$ produced by oxidation of glucose in the presence of glucose oxidase, the technique consists in reacting the $H_2O_2$ with a fluorinated aromatic compound in the presence of peroxidase so as to release fluorine ions, which are then determined electrometrically by means of an electrode specific to these ions.

It was therefore tempting to combine the $H_2O_2$-forming reaction described in document EP-A-124 909 with the fluorometric determination of $H_2O_2$ described in document EP-A-20 623. Surprisingly, however, it was found that this combination is not possible directly, in view of the following findings:

(1) In the presence of metal ions in the concentration recommended in document EP-A-124 909 (5 mmol/1; page 9, line 6) the activity of peroxidase is normally inhibited with regard to its catalytic action on the breakage of the C—F bond and this inhibiting effect has to be neutralized by adding an activator such as 4-aminoantipyrine.

(2) In the absence of metal ions, or at least in the presence of very small quantities thereof (of the order of 1,000 less than the quantities recommended in document EP-A-124 909 or less, i.e. under conditions where it has been accepted that $H_2O_2$ is not quantitatively formed) it has surprisingly been discovered that NADH or NADPH co-enzymes can be quantitatively determined by the breakage reaction of the C—F bond to fluoride in the presence of peroxidase (without adding antipyrine, which on the contrary has an inhibiting effect in the presence case). We therefore have a new kind of reaction not involving the intermediate quantitative formation of hydrogen peroxide as in the prior art. This has also been confirmed by adding an enzyme such as catalase to the analytical medium, thus using up the $H_2O_2$ as soon as it is formed. Thus, the addition of catalase to the reaction medium as recommended by document EP-A-124 905 ($[Mn^{+2}] \sim 10^{-2}M$) results in a decrease of about 70% in the efficiency of breaking the carbon-fluorine bond, whereas the effect of catalase is negligible in a corresponding medium but containing $10^{-5}M$ of $Mn^{+2}$.

The aforementioned discoveries have thus led to the use of a new, unexpected technique for determining co-enzymes containing nicotinamine in general. This technique has resulted in the method according to the invention as defined in the accompanying claim 1. One advantage of the method is that co-enzymes can be determined in the presence of reagents which inhibit the formation of $H_2O_2$. The term "substances having peroxidase activity" means all substances having catalytic properties similar to those of peroxidase, inter alia haemoglobin and its derivatives (see BOYER et al., "The Enzymes" 8 (1963) Academic Press).

Of course, an electrometric method as disclosed in document EP-A-20 623 will preferably be used for determining the fluoride ion released by this method. However, any other technique for determining fluoride may be equally suitable.

The general principle of the present method can be briefly described as follows. The basic system according to the invention consists in adding an excess of an aromatic fluorine compound and peroxidase to a buffer medium containing the reduced co-enzyme to be determined, and then to agitate the medium in the presence of air. The result is a breakage of the F—C bond in the fluorine compound and corresponding release of $F^-$ ions at a reaction rate proportional to the quantity of co-enzyme present. There is also a stoichiometric factor between the quantity of fluoride ions released and the quantity of co-enzyme to be determined. Analytically, however, this relation is less interesting since the reaction slows down considerably after a vigorous start and it is inconvenient to make "end-point" type measurements. However, "fixed-time" analysis would be possible by determining the reactions after a given time, which would always be the same for a set of analyses of the same type. In general, however, it is preferable to measure the release rates of $F^-$ ions under well-standardized conditions in order to obtain good reproducibility of measurements. For example, the measurement of the gradients of the rate curves (which of course depend on certain reaction parameters as well as on the concentration of substance to be measured) will advantageously be made after a certain latency time (incubation), the time being kept the same during a set of comparative tests. However, the latency time may be slightly different from one analysis to the other, since the maximum speed is obtained more quickly when the NADH concentration is higher. The buffers can be the usual buffers at pH 5 to 7.5, inter alia acetate, "tris", cacodylate, etc. The latter is preferred since it can rapidly stabilize the response of the fluorine electrode. It has also been found that the reaction rate (the breakage of the C—F bond) depends on the dimethylarsenate concentration in the buffer. Preferably the cacodylate buffer has a molar concentration of 0.05 to 0.5 M.

The concentration of released $F^-$ ions is preferably determined by using an electrode sensitive to $F^-$ ions but inert towards to other kinds of ions. The electrode may advantageously be an electrode selective to $F^-$ ions and of type 96-05 produced by ORION RESEARCH INC. Cambridge. Mass. USA. Other electrodes may be equally suitable, however, All details regarding use of these electrodes for determining $F^-$ ions may be found in the aforementioned document EP-A-20 623.

The present method, of course, is also of use for determining all additional constituents capable of quantitatively reacting in the presence of nicotinamide co-enzymes (in reduced or oxidized form) thus resulting in a variation (measurable by the present method) in the reduced form occurring in the medium.

For example, when the present reaction medium is used for determining precursor systems, i.e. systems where the quantitative formation of co-enzyme depends on one or more successive conversions of a substance to be measured, the technique required is quite similar to that described hereinbefore. The reason (and this is a significant advantage of the invention) is that the detection and electrochemical measurement of fluoride ions is unaffected by the presence of numerous other factors and substances dissolved in the reaction medium. Also, the present process is of direct use for measuring glucose and urea by method similar to those mentioned in the introduction.

Glucose, for example, is determined by first converting it to glucose-6-phosphate in the presence of ATP and hexokinase (or another enzyme having similar properties), after which a known quantity of NADP is added and the previously-mentioned process is used to measure the NADP formed during conversion of glucose-6-phosphate to glucono-δ-lactone-6-phosphate in the presence of G6PDH. At the beginning of the reaction, the reaction medium does not contain NADH, which appears during the enzymatic process. Actually the two reactions, that catalyzed by hexokinase and that catalyzed by G6, occur simultaneously in the presence of $NAD^+$ and ATP. The formation of NAD is therefore continuously measured from the beginning of the reaction.

Similar considerations apply to all other cases of biochemical reactions involving the present coenzymes either as starting products or as reaction products. One example is the determination of urea.

A sample of urea taken from a biological fluid such as urine or blood plasma and mixed with a suitable buffer is mixed with an excess of urease, oxoglutarate and GLDH accompanied by the fluorine compound and an exactly known quantity of NADH (also in excess but of the same order of magnitude as the urea to be measured, to avoid problems of disproportion). Next, after waiting a certain time for NADH to be converted to NAD+, the F− ion electrode is inserted into the mixture, which is agitated in air. A catalytic quantity of peroxidase (POD) is then added and the variation in electrode potential with time is measured, in order to determine the quantity of NADH not used during the reaction and consequently deduce the quantity of urea in the sample for analysis.

Document EP-A-20 623 gives details of the technique using the fluorine electrode and the physical and chemical considerations in interpretation of the results.

Briefly, a standard curve is preferably referred to in order to determine the release rate of F− ions after reaction of an unknown sample. A standard curve can be obtained as described hereinbefore by determing a set of samples containing known concentrations of coenzyme. The release rate of F− ions is recorded for each sample and the gradient of the kinetic curves is measured at a time (the same of course for each sample) when the rate curves are almost straight lines. The gradients are then shown on a graph in relation to the concentrations of coenzymes, so as to obtain a standard reference curve. The measured electrometric parameters used for preparing the kinetic curves can be the voltage readings of the electrometric system used together with the fluorine electrode (mV), or preferably the corresponding values of [F−] which can be calculated by the Nernst equation, which in the present case has the following form:

$$E = E' - S \cdot \log[F^-]$$

where E is the measured voltage and E' is an experimentally determined constant belonging to the system and including the activity factors and potentials of liquid junctions. S is the "Nernst gradient" which is a constant equal to about 57.5 mV (in the cacodylate buffer at pH 7.5) for a variation of 10 units in the F− concentration, the latter being expressed in mols/l. If the [F−] values calculated from the above relation are used in the speed graphs instead of the values in mV, the resulting curves are closer to straight lines and their gradient is easier to establish, so that more accurate reference graphs can be drawn.

The following are examples of aromatic compounds fluorinated on the ring and suitable for the present invention: 2-, 3- and 4-fluorophenols, tetrafluorophenol, pentafluorophenol and p-fluoroaniline; 4- and 2-fluorophenol are preferred.

Furthermore, the minimum proportion of co-enzyme detectable and measurable by this method can be reduced by adding a small quantity of manganese II ions to the reaction medium. This addition, however, is useful only when the concentration of co-enzyme is very low and near or below the lower limit normally accessible without manganese. For example it is useful to add $Mn^{++}$ (concentration from $2 \times 10^{-6}$ to $10^{-4}$M) when the quantities of co-enzyme are of the order of $10^{-4}$ to $10^{-5}$M. In such cases the practical reaction rate can be multiplied by a factor of about 5. In the presence of a higher concentration of co-enzyme, the presence of $Mn^{+2}$ ions will be accompanied by a defect in linearity tending to reduce the accuracy of measurement. Consequently when the concentrations of co-enzyme to be determined are above $10^{-4}$, it may be preferable not to use manganese.

The following examples, which illustrate the invention in greater detail, will be more clearly understood from the accompanying drawings in which.

EXAMPLE 1

Determination of NADH at pH 7.5

Figure 1:
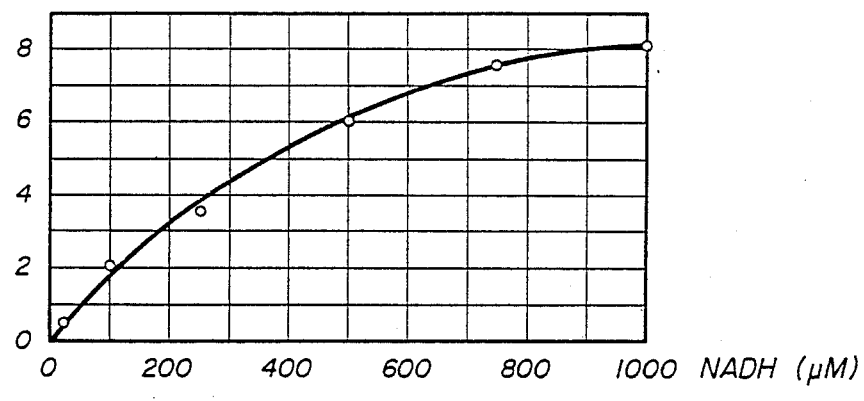
FIG. 1 is a graph representing the variation in the amount of NADH in dependence on the release rate of F− ions at pH 7.5.

This determination according to the invention was made in a buffer solution. Preferably the conventional cacodylate buffer is used. Phosphate buffers at pH 7-7.5 are also suitable but in that case the measuring electrode (when F− is determined electrometrically) is more difficult to stabilize and calibration by means of known solutions of NaF is less accurate and reproducible. The "tris" buffer is also suitable between 7 and 7.5.

(a) Preparation of cacodylate buffer: 21.41 g of sodium dimethylarsenate trihydrate (MERCK) was dissolved in 800 ml of twice-distilled water. 1 ml of a $5 \times 10^{-3}$M solution of manganese (II) chloride and 2 ml of a $10^{-3}$M solution of NaF was then added. The pH was then brought to exactly 7.5 with 1N HCL and the level was made up to 1 litre with twice-distilled water.

(b) Reaction medium for analysis: 0.112 g of p-fluorophenol (EGA-CHEMIE) was dissolved in 100 ml of cacodylate buffer (a) as hereinbefore. Since pfluorophenol always contains a small quantity of F−, the concentration of fluoride ion in medium (b) is of the order of $3-5 \times 10^{-6}$M.

(c) Peroxidase solution: horseradish peroxidase (BOEHRINGER; RZ 3.0; 250 U/mg) was used. A suitable quantity was dissolved in buffer (a) as hereinbefore in order to obtain a solution containing about 0.4 g/l (100 U/ml);

(d) Standard solutions of NADH: the disodium salt of NADH (SIGMA), theoretical molecular weight 7.5 D, was used. It was dissolved in cacodylate buffer (a) so as to obtain a titrate solution of 38 g/l ($5 \times 10^{-2}$M). Next, the same buffer was used for dilution to prepare standard solutions containing 3.75, 2.25 and $1.25 \times 10^{-2}$M; 5 and $1.25 \times 10^{-3}$M and $5 \times 10^{-4}$M.

(e) Analysis: the laboratory vessel used was a 10 ml mechanically-agitated polypropylene beaker. 4.8 ml of reaction medium (b) was placed in the beaker followed by 0.1 ml of solution (c). The buffer (a) alone was used as the solution with zero concentration of NADH. An electrode specifically sensitive to F− ions (type Orion 96-09; Orion RESEARCH, Cambridge, Mass., USA comprising its own reference diode) was immersed in the medium and was connected to a conventional electrometer (KEITHLEY Electrometer, Cleveland, Ohio, USA).

After the apparatus had been switched on, the assembly was left to stabilize for 3 minutes at ambient temperature with agitation, then 0.1 ml of one of the standard NADH solutions (d) was added. The release rate of F− ions was then measured for about 3 minutes by the aforementioned reaction, using a recorder to record the corresponding electrode potential. The recorded data were also transferred to a computer which supplied the gradient of the rate curve in its most linear region (after about 20 seconds and for about 30 seconds to one minute, these parameters of course being kept constant during the total standardization phase and during subsequent analaysis of unknown solutions).

The measured values (S) expressed directly in μ mols of $F^-$ released per minute as per the aforementioned formula, are as follows:

| Concentration of NADH (μ mols) | Gradient of rate curve (S) μM ($F^-$)/min |
|---|---|
| 0 | 0 |
| 10 | 0.236 |
| 25 | 0.512 |
| 100 | 2.058 |
| 250 | 3.498 |
| 500 | 5.976 |
| 750 | 7.581 |
| 1000 | 8.082 |

The graph based on the values hereinbefore is shown in FIG. 1.

Unknown solutions of NADH were analyzed exactly as described hereinbefore. After determining the gradient of the reaction curve, the desired value was obtained from the standard graph in FIG. 1. In practical chemical analysis, of course, these results are directly supplied by the computer.

EXAMPLE 2

Determination of NADH at pH 5.5

The method was as in Example 1 but with the following differences:

(a) The cacodylate buffer (0.1M) was identical with Example 1 except that its pH had been adjusted to 5.5 with 1N HCl.

(b) The reaction medium contained 0.01M of 4-fluorophenol 4FP.

(c) Peroxidase solution: solution containing 300 U/ml (about 1.2 g/l).

(d) Standard solution: these solutions were calculated so that 0.1 ml (the amount taken) contained the following quantities of NADH (in μM) in succession: 0, 25, 50, 75, 100, 125, 150, 175, 200.

Figure 4:
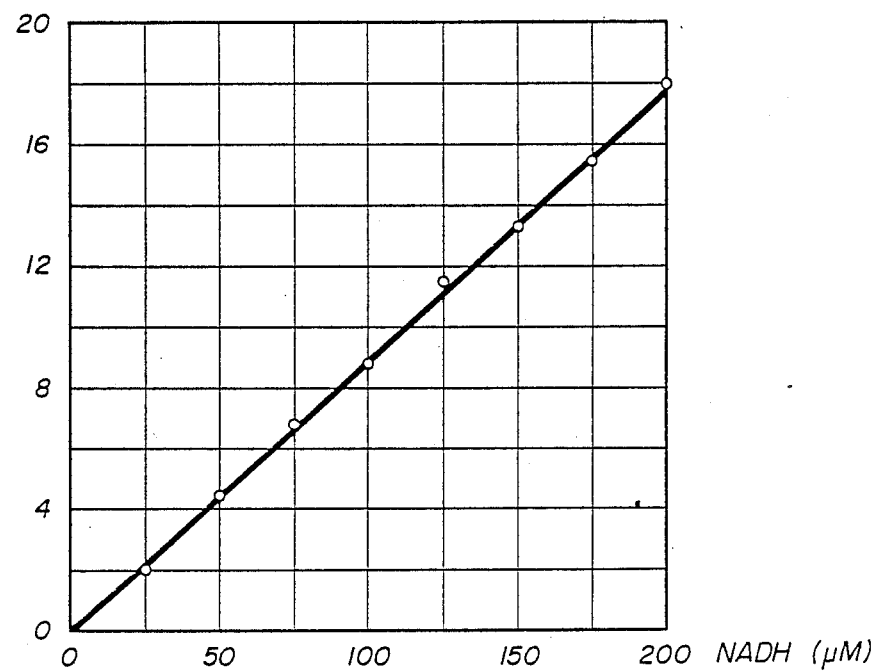
FIG. 4 is a graph similar to FIG. 1 but relating to pH 5.5.

The analysis was made as described in Example 1. The reaction, however, was more rapid and the effective gradient of the rate curve was remarkably constant, as early as 30 seconds after addition of NADH. The results are shown hereinafter and in FIG. 4.

| /NADH/ (μ mols) | Rate ([$F^-$] / μM/l/min) |
|---|---|
| 0 | 0 |
| 25 | 2.04 |
| 50 | 4.41 |
| 75 | 6.74 |
| 100 | 8.80 |
| 125 | 11.28 |
| 150 | 13.33 |
| 175 | 15.45 |
| 200 | 18.01 |

EXAMPLE 3

Determination of glucose

The determination was made as per the following diagram (see Notice: Test Glucose Rapide, ROCHE, DIAGNOSTICA):

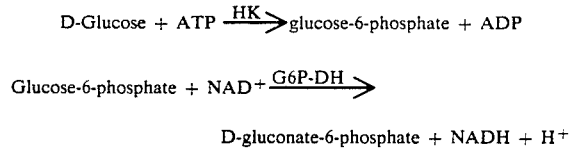

ATP = adenosine triphosphate
HK = hexokinase
ADP = adenosine diphosphate
G6P-D = glucose-6-phosphate dehydrogenase.

(a) Cacodylate buffer: same as in Example 1.
(b) Reaction medium: 1 portion of product No. 0711004 was dissolved in 24.5 ml of buffer (a), the product being supplied by Messrs. ROCHE and containing >50 μmols of $ATP^+$; >50 μmols of $NAD^+$; >7 U of HK, and >8 U of G6P-DH. 0.5 mol of peroxidase solution (C) in Example 1 and 28 mg of p-fluorophenol were then added. In the resulting solution, the reagents had the following concentrations: ATP $2 \times 10^{-3}$M; $NAD^+$ $2 \times 10^{-3}$M; HK 0.28 U/ml; G6P-DH 0.32 U/ml.
(c) Standard glucose solution: solutions of 0.5, 1, 2, 3, 4 and 5 g/l in 0.1% aqueous benzoic acid were used.

The analysis was made as described in Example 1, using 4.9 ml of reaction medium and 0.1 ml of standard solution (c) added after a stabilization period of 3 minutes. The results are given hereinafter and in FIG. 2.

Figure 2:
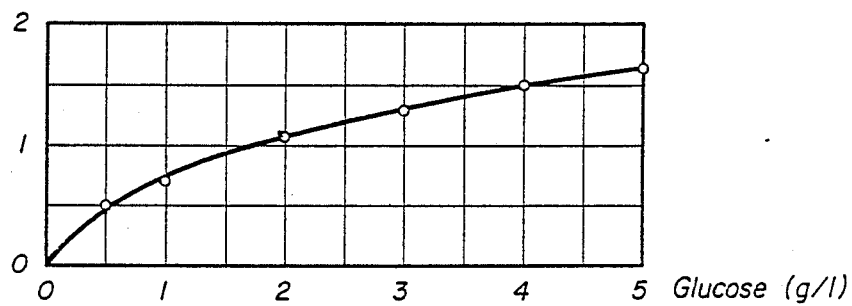
FIG. 2 is a graph similar to FIG. 1 but relating to the analysis of glucose.

The curve in FIG. 2 was used to compare the kinetic values obtained from unknown glucose solutions with the effective concentration of glucose in these solutions.

| Concentration of glucose (μ mols) | Rate (μmols $F^-$/l/min) |
|---|---|
| 0 | 0.09 |
| 55.5 | 0.50 |
| 111 | 0.69 |
| 222 | 1.08 |
| 333 | 1.29 |
| 444 | 1.50 |
| 555 | 1.65 |

EXAMPLE 4

Determination of urea

This reaction is based on the following diagram (see "Urea UV Test" by ROCHE DIAGNOSTICA):

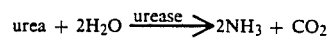

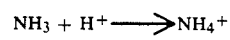

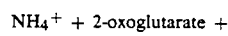

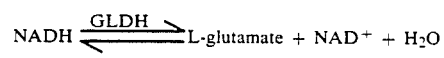

GLDH = glutamate dehydrogenase (a) Cacodylate buffer: same as buffer (a) in Example 1.

(b) Reaction medium: one portion of a mixture of enzyme and substrate of product No. 0713228 were dissolved in 30 ml of buffer (a), the product being supplied by Messrs. ROCHE (reagent kit for the kinetic determination of urea in serum). The portion contained: >25 U of urease, 197 μmols of 2-oxoglutarate, and 6 μmols of NADH. 33.7 mg of p-fluorophenol and 0.2 ml of a solution of GLDH (∼50 U) were also added. Medium (b) consequently contained the following reagents at the following concentrations:

0.83 U/ml urease; $6.57 \times 10^{-3}$M of 2-oxoglutarate; $2 \times 10^{-4}$M NADH and 3.33 U/ml GLDH (c) Peroxidase solution: same as the 100 U/ml solution described in Example 1.

(d) Standard urea solution: urea solutions were prepared in a physiological phosphate buffer, pH 6.7, at the following concentrations:

7.13; 4.99; 3.56; $1.426 \times 10^{-3}$M.

The analysis procedure was as in Example 1, using 3.82 ml of reaction medium (b) and 0.1 ml of the standard urea solution. The mixture of reagents, except for the peroxidase, was agitated (using the electrode) for 10 minutes, after which 0.08 ml of peroxidase solution was added. Measurement was then started and the rates were calculated after 20 to 30 seconds. The results are given hereinafter and in the graph in FIG. 3.

As can be seen, in this test the NADH was determined as it appeared during the reaction. This was the reason for providing an incubation time of 10 minutes. It was found that analysis is still valid though less efficient with incubation times of only 3 minutes.

| Concentration of urea in the standard solution ($10^{-3}$M) | Quantity of urea in the measurement ($\chi \times 10^{-6}$ mols) | Rate (μmols F$^-$/l/mi) |
|---|---|---|
| 0 | 0 | 0.91 |
| 1.426 | 35.6 | 0.81 |
| 3.56 | 89 | 0.67 |
| 4.99 | 125 | 0.58 |
| 7.13 | 178 | 0.46 |

Figure 3:
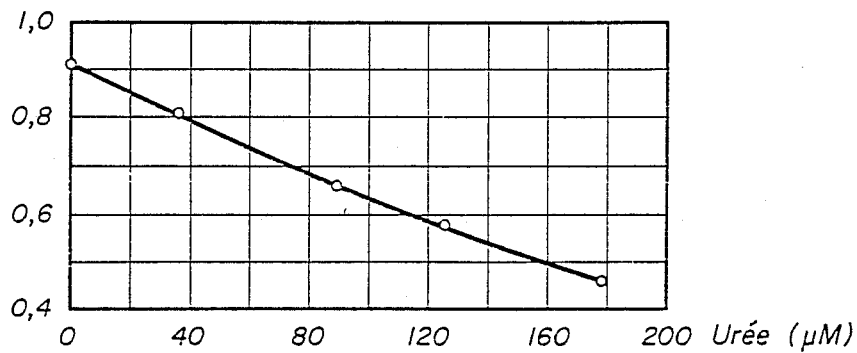
FIG. 3 is a graph similar to FIG. 1 but relating to the analysis of urea.

The graph in FIG. 3 was used to determine, by comparison, the urea concentration in unknown samples which had been subjected to the analysis procedure described hereinbefore.

EXAMPLE 5

Determination of NADH in the presence of various organofluorine compounds (a) A cacodylate buffer identical with buffer (a) in example 1 was used.

(b) A set of reaction media were prepared by proceeding as described in the case of solution (b) in Example 1, so as to obtain $10^{-2}$M solutions of the following organofluorine compounds in buffer (a): 4-fluorophenol (4FP); 3-fluorophenol (3FP); 2-fluorophenol (2FP); tetrafluorophenol (TFP); pentafluorophenol (PFP).

(c) A peroxidase solution identical with solution (c) in Example 1 was used.

(d) A $5 \times 10^{-2}$M solution of NADH in buffer (a) was used (see solution d) in Example 1).

The analysis procedure was as described in Example 1, using identical quantities of reagents, 4.8 ml of reaction medium (b), 0.1 ml of solution (c) and 0.1 ml of solution (d).

The rate measurements are as follows:

| Organofluorine compound | μMF$^-$/min |
|---|---|
| 4FP | 4.00 |
| 3FP | 1.00 |
| 2FP | 2.65 |
| TFP | 0.71 |
| PFP | 2.62 |

As can be seen, 4FP gave the most sensitive measurement.

Tests were made with solutions of non-horseradish peroxidase. All these solutions were positive. Note also that the purity of a peroxidase such as horseradish peroxidase may vary appreciably with its origin. The purity is represented by an RZ (Reinheitzahl) coefficient relating to optical absorption measurements:

$$RZ = \frac{A\ 403\ nm}{A\ 275\ nm}$$

RZ may be equal to 3 for products having maximum purity. By way of example, the RZ values for the following peroxidases are:

| | RZ |
|---|---|
| SIGMA peroxidase | 0.64 |
| MILES LAB. peroxidase | 1.25 |
| BOEHRINGER, Mannheim Peroxidase | 3.0 |

The procedures for measuring other nicotinamide co-enzymes, inter alia NADPH and APADH, in other cases involving these co-enzymes, are identical with that described hereinbefore.

EXAMPLE 6

Determination of effect of catalase

Using the same method as described in the preceding Examples, a known quantity of NADPH solution was added to a reaction medium prepared in a "tris" buffer, pH 7.4, 0.05M. The first reaction medium (A) was prepared so as to contain a concentration of metal ions corresponding to the description in document EP-A-124 909:

| Mn$^{++}$(in sulphate form) | $10^{-2}$ M |
|---|---|
| AAP (4-aminoantypyrine) | $5 \times 10^{-4}$ M |
| POD (peroxidase) | 6 U/ml |
| NADH | $10^{-4}$ M |

The mixture was left to incubate and after a given time (20 seconds in case A1 and 2 minutes in case A2) a quantity of p-fluorophenol (FP) was added such that the solution contained 10 mM of this reagent. The release rate of the fluorine ion was then recorded as described in the preceding examples.

The tests were repeated under identical conditions but after adding a quantity of catalase to the medium such that it contained 275 U/ml (in cases AC1 and AC2).

A second reaction medium (B) was prepared under the conditions according to the invention:

| | |
|---|---|
| Mn$^{++}$ | $10^{-5}$M |
| AAP | — |
| POD | 2 U/ml |
| NADH | $10^{-3}$M |

The same procedure was used with the same quantity of p-fluorophenol added after the same latency time (B1 and B2) and with 255 U/ml of catalase in a second test (cases BC1 and BC2).

The resulting reaction rates (in arbitary comparative units) are as follows:

| Test | Speed | Catalase |
|---|---|---|
| A1 | 7.1 | No |
| A2 | 7.6 | No |
| AC1 | 2.3 | Yes |
| AC2 | 2.5 | Yes |
| B1 | 3.0 | No |
| B2 | 3.0 | No |
| BC1 | 3.0 | Yes |
| BC2 | 2.7 | Yes |

It can be seen that, whereas in case (A) there is a considerable decrease in the formation of $H_2O_2$ in the presence of catalase, the influence of catalase on the reaction according to the invention is negligible.

In cases A1 and A2 the reaction rate is greatly reduced when operating in a medium without aminoantipyrine (AAP), indicating that this substance acts as an activator. Exactly the contrary applies to cases B, when the difference is much less clear. Consequently, under the operating conditions recommended by document EP-A-124 909, direct determination of $H_2O_2$ by simple replacement of the traditional colorimetric method by fluorometric determination as per document EP-A-20 623 does not give the results expected from this juxtaposition. To obtain optimum results it is necessary to work in the presence of an activator such as AAP and in the absence of catalase or any other factor capable of consuming the $H_2O_2$ formed.

EXAMPLE 7

Comparisons between the method according to the invention and the method in document EP-A-124 909

The procedure under the general conditions in Example 6, using a "tris" buffer, were used on a sample of $2 \times 10^{-4}$M of NADH in the presence of 6 U/ml POD, variations being made in the pH, concentration of Mn$^{+2}$ ions and the presence or absence of 4-aminoantipyrine. The operating conditions and the results in the form of corresponding reaction rates (expressed in $\mu$mols of F$^-$/1/min) are shown hereinafter.

| Concentration Mn$^{+2}$(M) | pH | 4-AAP | /F$^-$/$\mu$mol/1/min |
|---|---|---|---|
| $10^{-2}$ | 7.5 | $5 \times 10^{-4}$ | 27 |
| $10^{-2}$ | 7.5 | 0 | 0.27 |
| $10^{-5}$ | 7.5 | $5 \times 10^{-4}$ | 0.04 |
| *$10^{-5}$ | 7.5 | 0 | 5.3 |
| $10^{-5}$ | 5.5 | $5 \times 10^{-4}$ | 7.2 |
| *$10^{-5}$ | 5.5 | 0 | 54.2 |

*Tests as per the invention

These results clearly show the advantages of the invention compared with the citation, i.e., greater sensitivity at pH 5.5, and an inhibiting effect of 4-aminoantipyrine in the presence of a small proportion of manganese, whereas the contrary effect occurs at higher concentrations of manganese ($10^{-2}$M) i.e. under conditions where the formation of $H_2O_2$ predominates.

EXAMPLE 8

Comparative performance of various fluorinated aromatic compounds at pH 5.5

The method was similar to Examples 2 and 5, using the following reagents:

(a) Cacodylate buffer: as in Example 2, 0.1M, pH 5.5.

(b) Reaction medium: 0.425 mmols of the fluorine compound mentioned hereinafter was dissolved in about 40 ml of buffer (a), 0.2 ml of $10^{-3}$M NaF solution was added and the solution was made up to 50 ml with buffer (a). Concentration of F$^-$ = $4 \times 10^{-6}$M. The following fluorine compounds were used:
  b1: 4-fluorophenol (56 mg) 4-FP;
  b2: 4-fluoroaniline (55.5 mg) 4-FA;
  b3: tetrafluorophenol (83 mg) TFP;
  b4: pentafluorophenol (92 mg) PFP.

(c) $10^{-3}$M solution of MnCl$_2$ in twice-distilled water, (d) 600 U/ml solution of peroxidase (POD) in a 0.01M acetate buffer at pH 5.5 (100 U/mg SIGMA peroxidase)

(e) $5 \times 10^{-2}$M solution of NADH in a 0.05M "Tris" buffer at pH 7.5

The measurement was made as follows: 4.85 ml of solution (b), 0.05 ml of solution (c) and 0.05 ml of peroxidase solution (d) were placed in a polyethylene beaker (10-ml). The fluorine electrode was immersed in the solution, which was magnetically agitated, the apparatus was left to stabilize for 1 minute, then 0.05 ml of NADH solution (e) were added.

Since the measurement was comparative, in this test we were content to measure the quantity of F$^-$ released 1 minute after adding solution (e) (the "fixed-time" measuring technique.)

The results, given in the Table hereinafter in dependence on the nature of the fluorine compound used, show that at pH 5.5, PFP gives the most sensitive tests:

| Fluorine compound | F$^-$($\mu$m) |
|---|---|
| 4-FP | 17.9 |
| 4-FA | 9.1 |
| TFP | 57.7 |
| PFP | 62.7 |

We claim:

1. An analytical method of determining a nicotinamide co-enzyme selected from the group consisting of NADH, NADPH and APADH wherein the co-enzyme is reacted in a reaction medium with a fluorinated-ring aromatic compound selected from the group consisting of 2-, 3- and 4-fluorophenol, tetrafluorophenol, pentafluorophenol and 4-fluoro-aniline in the presence of oxygen and a substance having peroxidase activity, this reaction resulting in the formation of fluoride ions which are determined, the rate at which the ions are formed being quantitatively linked to the original quantity of co-enzyme to be determined.

2. A method according to claim 1, the reaction medium contains at least one additional constituent capable of quantitatively reacting in a chain reaction involving NAD/NADH coenzyme systems, the method adapted for determining the additional constituent.

3. A method according to claim 1, wherein the fluoride ions are determined electrometrically by means of an electrode which is specific to said ions.

4. A method according to claim 3, wherein a buffer at pH 5-7.5 is used.

5. A method according to claim 4, wherein the buffer is "tris" or acetate.

6. A method according to claim 4, wherein a cacodylate buffer is used at a molar concentration of 0.05 to 0.5M, the reaction rate depending on the concentration of dimethylarsinate in the buffer.

7. A method according to claim 4, wherein $Mn^{++}$ ions in a concentration of $2\times10^{-6}$–$10^{-4}$M are added to the reaction medium.

8. A method according to claim 3, wherein it is used for determining glucose in samples of biological fluids, the glucose reacting with ATP in the presence of hexokinase to give glucose-6-phosphate which is oxidized by $NAD^+$ in the presence of glucose-6-phosphate dehydrogenase to D-gluconate-6-phosphate with corresponding production of NADH in direct proportion to the glucose to be measured.

9. A method according to claim 3, wherein it is used for determining urea in biological fluids, which supply ammonia by hydrolysis in the presence of urease, the ammonia supplying L-glutamate by reaction with 2-oxoglutorate in the presence of glutamate dehydrogenase and NADH, the consumption of the latter being in direct proportion to the urea to be measured.

10. A method according to claim 1 wherein the substance having peroxidase activity is peroxidase enzyme.

* * * * *